United States Patent [19]

Goodwin

[11] Patent Number: 4,901,727
[45] Date of Patent: Feb. 20, 1990

[54] MICRO-PROBE FOR GAS SAMPLING

[75] Inventor: Brian Goodwin, Mountainside, N.J.

[73] Assignee: The BOC Group, Inc., New Providence, N.J.

[21] Appl. No.: 190,549

[22] Filed: May 5, 1988

[51] Int. Cl.$^4$ .............................................. A61B 5/00
[52] U.S. Cl. ....................................... 128/632; 604/43
[58] Field of Search .................... 128/632, 635, 637; 604/43, 93, 103; 55/16, 158, 270

[56] References Cited

U.S. PATENT DOCUMENTS

| | | | |
|---|---|---|---|
| 3,572,315 | 3/1971 | Cullen | 128/632 |
| 3,893,448 | 7/1975 | Brantigan | 128/632 |
| 3,952,730 | 4/1976 | Key | 128/632 |
| 3,981,297 | 9/1976 | Dunn et al. | 128/632 |
| 3,983,864 | 10/1976 | Sielaff et al. | 128/632 |
| 4,016,863 | 4/1977 | Brantigan | 128/632 |
| 4,016,864 | 4/1977 | Sielaff et al. | 128/632 |
| 4,244,713 | 1/1981 | Goodwin | 128/632 X |
| 4,274,417 | 6/1981 | Delpy | 128/632 |
| 4,340,615 | 7/1982 | Goodwin et al. | 128/632 X |
| 4,516,580 | 5/1985 | Polanyi | 128/632 |

Primary Examiner—Angela D. Sykes
Attorney, Agent, or Firm—Larry R. Cassett; Roger M. Rathbun

[57] ABSTRACT

A catheter probe for use in the analysis of gases absorbed in liquids, particularly suitable for the in vivo analysis of blood gases, the probe includes an equilibration chamber disposed within the active length of the probe at the distal end of the probe and which is surrounded by a gas permeable membrane. A carrier gas is introduced into the probe and enters the equilibration chamber where the gas sought to be analyzed from the blood equilibrates with the carrier gas and forms a bolus of sample gas. That bolus is then caused to flow out of the probe to an analyzer. The equilibration chamber is formed of an elongated, tortuous path that allows a high surface area to unit volume ratio, that is, the ratio of the area of the equilibration chamber that is immediately beneath the gas permeable chamber to the volume of the flow path though the equilibration chamber is high. Preferable the equilibration chamber is formed as a spiral path. The cross-sectional area of the paths through which carrier gas passes through the catheter probe are designed to be substantially the same to minimize mixing of the bolus of carrier gas containing the blood gases with the non-equilibrated carrier gas.

11 Claims, 2 Drawing Sheets

MICRO-PROBE FOR GAS SAMPLING

BACKGROUND OF THE INVENTION

This invention relates to the sensing of gases dissolved in liquids and is specifically adapted for the in vivo sensing of blood gases. Blood gases have been sensed and analyzed by various prior art methods, one of which being disclosed in U.S. Pat. Nos. 3,983,864 and 4,016,864. As shown in those patents, a carrier gas is introduced into a special catheter probe, and held in a chamber where the blood gases equilibrate through a gas permeable membrane with the carrier gas and the carrier gas containing the equilibrated blood gases is thereafter withdrawn and analyzed.

The catheter is introduced in vivo into the particular blood vessel sought to be analyzed. An equilibration chamber is provided in the probe and allows an equilibration between the carrier gas passing through the probe and the blood gases contained in the blood. Equilibration occurs through a gas permeable membrane that surrounds the equilibration chamber and has its outside surface in direct contact with the blood to be analyzed. The blood gases pass into the equilibration chamber through the gas permeable material until the partial pressures within the chamber achieve blood levels.

The carrier gas remains in the equilibration chamber for a specific period of time to insure equilibration is completed, at which time, the carrier gas containing that bolus of carrier gas with the equilibrated blood gases is removed and its content determined by an analyzer such as a gas chromatograph.

A vacuum means is used to transport the bolus of equilibrated gases to the analyzer through various valving means.

One of the difficulties with such present systems is that a certain finite time is needed for the sample gas to fully equilibrate with the blood gases and thus, the number of samples one can take within any specific period of time is limited. That time is partially dependent upon the ratio of area of the equilibration chamber that directly receives the blood gases through the permeable material to the volume of the equilibration chamber as well as other factors such as the gas permeability of the membrane. To be effective and rapid, the aforementioned ratio should be high, that is, there needs to be a large surface area through which the blood gases pass into the equilibration chamber in relation to the volume of carrier gas in the chamber.

The equilibration chamber itself is normally located at the distal end of the catheter and it comprises an active length of the catheter at that distal end. Present catheters have a relatively long active length in order to include a sufficiently large equilibration chamber and therefore a technician utilizing the catheter may be unable to pinpoint the exact location in the blood vessel where the blood gases are being analyzed. It is therefore desirable that the active length of the catheter be minimized.

A further disadvantage of prior art catheters is in the carrier gas passing through the catheter through dissimilar pathway areas, that is, an internal mixing takes place when the pathway of the gas through the catheter passes from one cross-sectional area to another that is significantly dissimilar in size. A mixing occurs between the equilibrated bolus and its edges that are surrounded by the carrier gas so that the defined edges of the bolus itself are disrupted.

SUMMARY OF THE INVENTION

The catheter probe of the present invention comprises an annular inlet capillary that receives the carrier gas from the gas source and forms a path for that carrier gas to the distal end of the probe. At the distal end, the carrier gas enters the equilibration chamber that is surrounded by a gas permeable membrane and which is in contact with the liquid containing the dissolved gases to be analyzed. In the preferred embodiment, that gas permeable membrane is introduced directly into the patient's bloodstream.

The equilibration chamber comprises the active length of the catheter probe and comprises an elongated, tortuous path through which the carrier gas passes. As will be noted, the elongated, tortuous path is preferably a spiral path formed directly under the inner surface of the permeable membrane so that the equilibration chamber volume is constrained to be a thin layer (or shell) at the outer surface of the probe. As the carrier gas winds its way along the spiral equilibration chamber, its outside surface area is in contact with the gas permeable membrane and is relatively large in respect to the volume of carrier gas passing through the equilibration chamber.

Thus, the ratio of active surface area per unit of equilibration volume is high, in the order of 50:1 so that the rapidity of the equilibration process is enhanced.

In addition, since the carrier gas passes through an elongated, tortuous path as it passes through the active length of the catheter probe, considerably more equilibration surface area is made available to carry out the equilibration process per unit of linear catheter length. The active length of the catheter probe may be thus reduced, thereby allowing the user to more accurately ascertain the position within the patient's blood stream that is being analyzed. The length of the tortuous spiral path is important since it delineates the length of the blood gas bolus which enters the centrally disposed capillary outlet tube, (the transport capillary).

This bolus will be eroded by convection and diffusion effects which cause mixing with the carrier gas during transport through the outlet tube. The mixing effect is evident initially at the leading and trailing edges of the gas bolus; a minimum length of bolus (l) for initial partial pressure information to be preserved within the bolus center can be calculated from the relation:

$$l = \{4/3 * a^2 * U * L/D\}^{\frac{1}{2}}$$

where
  $a$ = radius of the outlet tube;
  $L$ = length of the outlet tube;
  $U$ = carrier gas velocity;
  $D$ = carrier/bolus coefficient of interdiffusion.

A further centrally disposed capillary outlet tube having an open end adjacent the distal end of the catheter probe receives the equilibrated carrier gas and through that capillary outlet tube, the equilibrated carrier gas bolus is withdrawn and directed to an analyzer.

As a further feature, the cross-sectional areas of the various paths through which the carrier gas passes as it progresses through the catheter probe are designed to be substantially equal, thus inadvertent mixing of the equilibrated carrier gas with the non-equilibrated carrier gas is minimized. More specifically, the cross-section area of the annular inlet capillary; the cross-section area of the elongated, tortuous path of the equilibration chamber and the cross-section area of the capillary outlet are substantially equal.

DESCRIPTION OF THE PREFERRED EMBODIMENT

Figure 1:
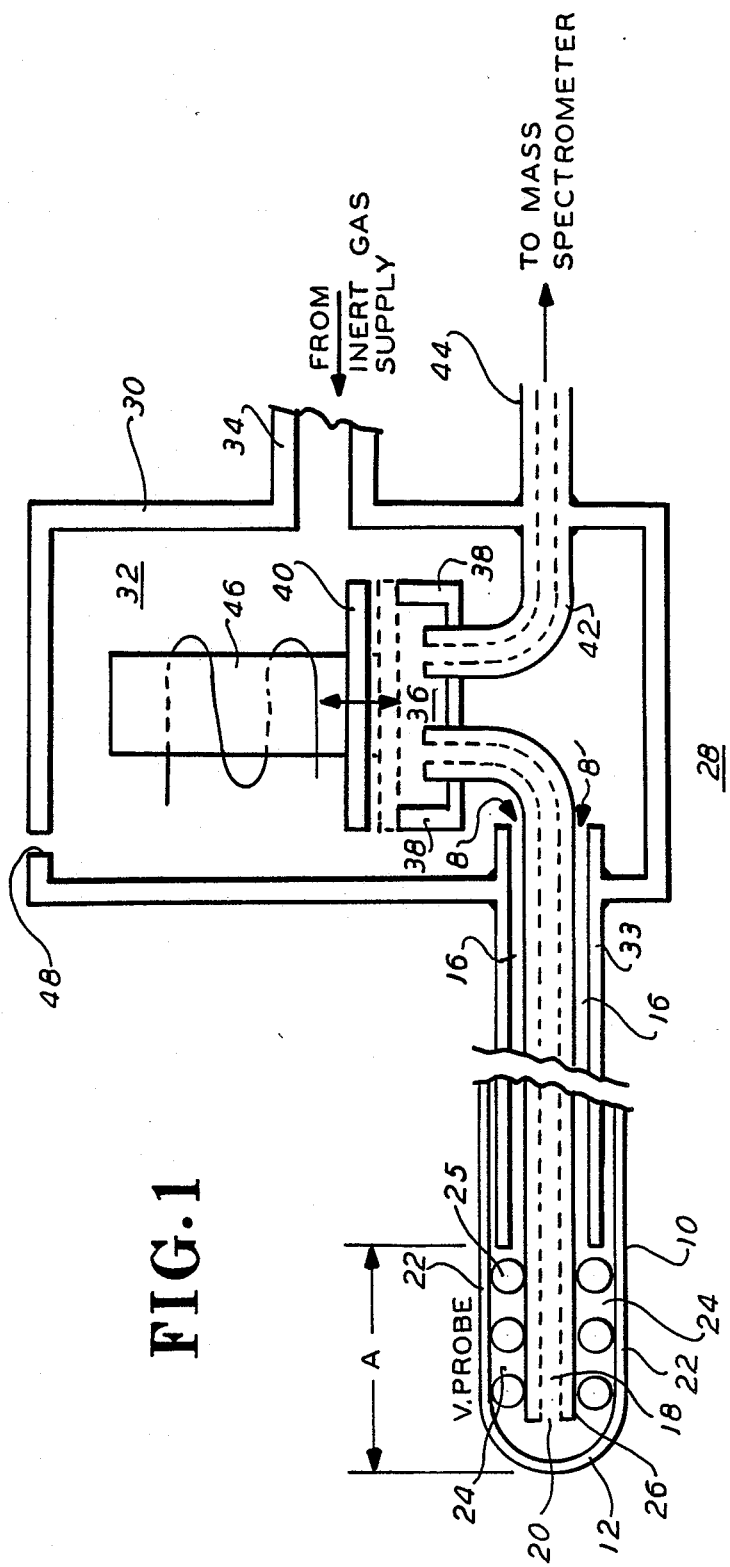
FIG. 1 is a schematic view showing the flow of carrier gas and its control for the system utilizing the present invention.

Referring first to FIG. 1, there is shown a schematic view of the overall gas analysis system for which the catheter probe of the present invention is useable.

In FIG. 1, catheter probe 10 is shown in schematic form, partially cut away, and having a distal end 12 that is inserted into the patient's blood stream to be analyzed. The catheter probe 10 comprises an annular capillary inlet 16 through which carrier gas is delivered to the catheter probe 10, as will be explained. An outlet capillary 18 having its open end 20 at or adjacent to the distal end 12 of the catheter probe 10 is provided and which withdraws carrier gas from the catheter probe 10.

A gas permeable membrane 22 makes up the exterior of the catheter probe 10 and, as will be explained, allows the blood gases to pass there through into the equilibration chamber 24, formed therein. As will be noted, the equilibration chamber 24 receives carrier gas from annular capillary inlet 16 and that carrier gas thereafter passes through the equilibration chamber 24 before entering the open end 20 of outlet capillary 18.

Equilibration chamber 24 is formed directly against the inner surface of gas permeable membrane 22 for reasons which will become apparent. A wire 25 is wound around the central conduit 26 in which outlet capillary 18 is formed. That part of the catheter probe 10 in which the equilibration chamber 24 is located is the active length and is indicated in FIG. 1 by the dimension A.

A valve 28 is used to control the introduction of gas to and remove gas from the catheter probe 10. A suitable valve for use with the present system is shown and described in U.S. Pat. No. 4,706,700 of Jumeau and therefore is described herein schematically only.

Valve 28 comprises an outer housing 30 forming therein a main chamber 32. An inlet 34 is provided in outer housing 30 and receives carrier gas from a suitable source (not shown). The preferred carrier gas is argon, however, other carrier gases, such as helium, may be employed. As noted, the carrier gas is thus introduced into main chamber 32 though inlet 34.

The main chamber 32 also communicates directly with annular capillary inlet 16 as further illustrated by reference to arrows B; annular capillary inlet 16 being formed between the outer diameter of central conduit 26 and the inner diameter of tubing 33 and, as noted, forms a path for the carrier gas to the equilibration chamber 24.

Valve 28 further includes an inner chamber 36 within main chamber 32 and inner chamber 36 is formed by fixed walls 38 and a moveable wall 40. As shown in the solid line position of FIG. 1, moveable wall 40 is displaced with respect to fixed walls 38 so that inner chamber 36 is open and readily communicates with main chamber 32.

As also noted, central conduit 26 is sealed to fixed walls 38 so that outlet capillay 18 communicates with the interior of inner chamber 36. A further capillary conduit 42 also communicates with the interior of inner chamber 36 and forms a path to an outlet conduit 44 leading to the exterior of main chamber 32 and, as will be explained communicates with an analyzer such as a mass spectrometer for analyzing gases.

A solenoid 46 is electrically energizable and de-energizable to move moveable wall 40 between its dotted line position seated against fixed walls 38, and its solid line position displaced from fixed walls 38 thus selectively closing or opening inner chamber 36 with respect to main chamber 32. A bleed vent 48 is also formed in outer housing 30.

Briefly then, the operation of the system can be described as follows. When the solenoid 46 is suitably energized, the moveable wall 40 is moved to its dotted line position closing inner chamber 36. In this position, carrier gas is continually drawn through the system, including catheter probe 10, by a slight vacuum drawn by the mass spectrometer acting at the outlet conduit 44. That vacuum draws the carrier gas from its source into main chamber 32 of valve 28 and thereafter sequentially through annular capillary inlet 16, equilibration chamber 24, outlet capillary 18, through inner chamber 36 and out through capillary conduit 42 to outlet conduit 44.

When it is desired to utilize the catheter probe 10 to take a sample of blood gases, solenoid 46 is activated to move moveable wall 40 to its solid line position opening inner chamber 36 to main chamber 32. Since inner chamber 36 is now fully open to main chamber 32, the vacuum drawn by the mass spectrometer draws carrier gas directly through inlet 34 and through capillary conduit 42 to outlet conduit 44, thereby by-passing any flow to catheter probe 10.

The carrier gas thus contained within capillary probe 10 is retained at a standstill and equilibration occurs through blood gases passing from the blood through gas permeable membrane 22 and into carrier gas in the equilibration chamber 24. After a sufficient period of time has elapsed to insure equilibration has been completed, the solenoid 46 returns the moveable wall 40 to its dotted line position, closing inner chamber 36 and again causing flow through the catheter probe 10. This time however, that flow of carrier gas from catheter probe 10 contains a bolus of carrier gas into which the various blood gases have equilibrated from the patient's blood. That bolus continues to the mass spectrometer where it is detected and the blood gases analyzed.

Figure 2:
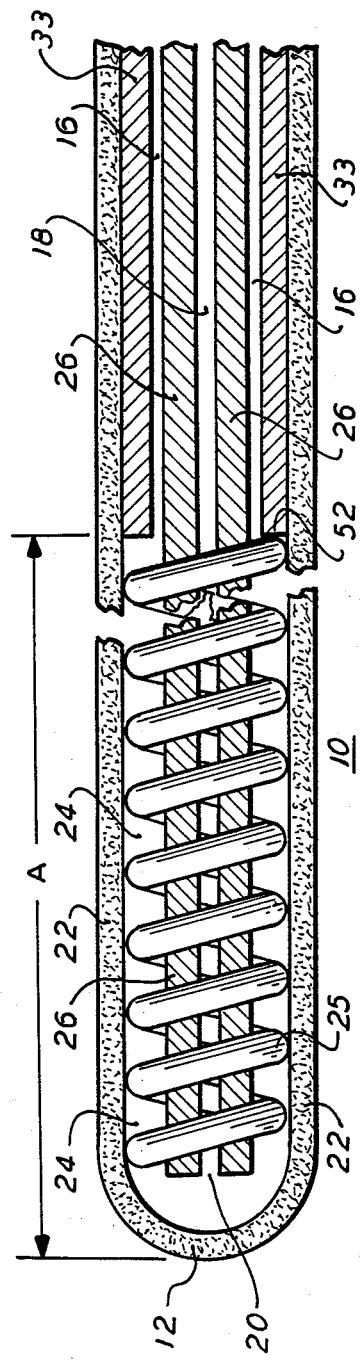
FIG. 2 is a cross-sectional view of the catheter probe of the invention showing, in particular, the active length thereof.
Figure 3:
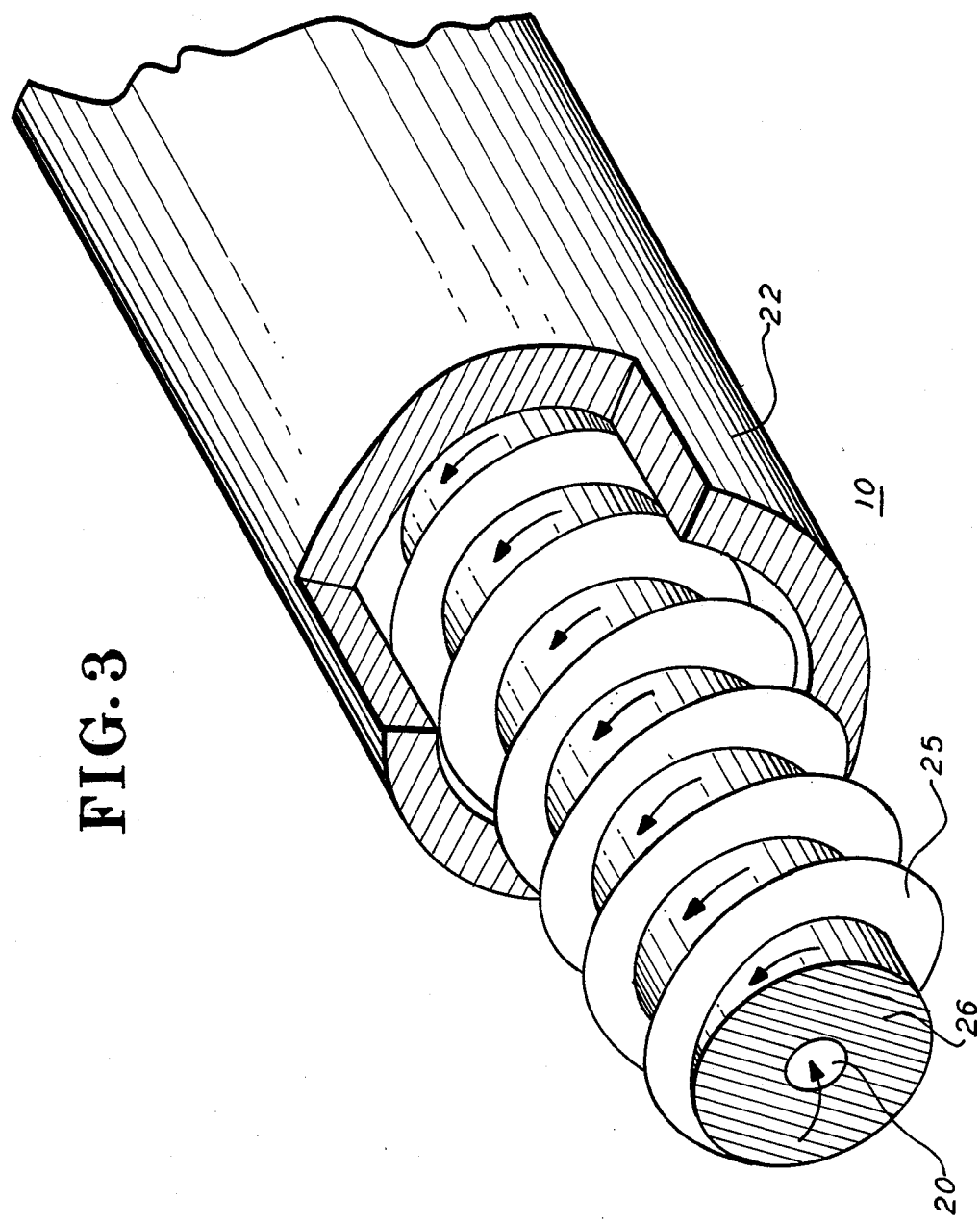
FIG. 3 is an isometric view, partly cut away, showing the components of the catheter probe constructed in accordance with the present invention.

Turning now to FIGS. 2 and 3, the details of the construction of the catheter probe 10 of the present invention can be explained.

Annular capillary inlet 16 is formed between the inner diameter of tubing 33 and the outer diameter of central conduit 26. Tubing 33 is preferably a commercially available polymer tubing, one example of which is suitable is crystaline polytrifluorochloro-ethylene available under the trademark Kel-F. The requirements of tubing 33 are that it provides some stiffening to the catheter probe 10 and yet is sufficiently flexible so as to be introducible along the interior of a patient's blood vessel. In the preferred embodiment, and to illustrate the size of the various components, tubing 33 has an outer diameter of about 0.250 millimeters (mm) and an inner diameter of about 0.160 (mm).

Central conduit 26 is preferably vitreous silica coated with several layers of a polyamide for mechanical strength and is commercially available from the Scientific Glass Engineering Co., of Australia. The material is utilized commercially for various fiber optic applications and is preferably of an outer diameter of about 0.150 mm, and an inner diameter of between 0.025 to 0.050 mm. The inner diameter of the central conduit 26 thus forms outlet capillary 18 and in the illustrative embodiment therefore has a cross-sectional area of about $2.0 \times 10^{-3}$ mm$^2$. The annular capillary inlet 16 dimensionally therefore has an outside diameter of 0.160 mm and an inside diameter of about 0.152 mm and thus can be calculated to also have a cross-sectional area of about $2.0 \times 10^{-3}$ mm$^2$.

The wire 25 is used to form the elongated tortuous path of the equilibration chamber 24. Preferably that wire 25 is wound spirally around the outside diameter of central conduit 26 beginning at the terminal end 52 of tubing 33 and continuing to the open end 30 of central conduit 26 adjacent the distal end 12 of catheter probe 10. Wire 25 is preferably of molybdenum and has a coating that inhibits the condensation of water such as gold. In the dimensions of the preferred embodiment, wire 25 has a diameter of about 0.05 mm and its pitch is about 0.10 mm. In construction, the wire 25 is tension wound about and is embedded to some extent in the polyamide coating on central conduit 26. As such, the cross sectional area of the elongated, tortuous path of the equilibration chamber 24 is about $2.5 \times 10^{-3}$ mm$^2$.

Around the outside of equilibration chamber 24 is secured the gas permeable membrane 22. The gas permeable member 22 may readily be made of silicone rubber having a thickness of about 50 microns.

As can now be seen, equilibration chamber 24 is, in effect, an elongated, tortuous path that leads from annular capillary inlet 16 to the outlet capillary 18 and along which the carrier gas is passed. Since the equilibration chamber 24 is in direct contact with the inner surface of gas permeable membrane 22, a considerable surface area is provided within the active length, dimension A, of the catheter probe. Thus the ratio of surface area to unit volume of carrier gas sample is relatively high; with the present given dimensions, that ratio is about 50:1. The active length dimension can thus be less than 5 centimeters, preferably less than about 2 centimeters and yet there is sufficient path length along the equilibration chamber 24 to fully effect the desired equilibration.

Also, in accordance with the preferred dimensions, the cross-sectional area of the annular capillary inlet 16, the elongated, tortuous path of the equilibration chamber 24, and the outlet capillary are substantially the same, accordingly the cross-sectional areas of the entire path for the carrier gas through the catheter probe 10 are substantially the same, thus mixing of the bolus containing the equilibrated sample and the carrier gas is reduced.

While the present invention has been set forth in terms of a specific embodiment, it will be understood that the blood gas analyzing probe herein disclosed may be modified or altered by those skilled in the art to other configurations. Accordingly, the invention is to be broadly construed and limited only by the scope and spirit of the claims appended hereto.

I claim:

1. A blood gas catheter probe having a distal end for introduction into a patient's blood stream; said catheter probe comprising:
    (a) an inlet for receiving a carrier gas;
    (b) an outlet for removing carrier gas and blood gas contained therein from said catheter probe;
    (c) an equilibration chamber at said distal end of said catheter probe forming a continuous gas flow path between said inlet and said outlet;
    (d) a gas permeable membrane affixed to said catheter probe and surrounding said equilibration chamber, said membrane adapted to contact the patient's blood and allow equilibration of blood gases passing through said membrane into said carrier gas within said equilibration chamber and carrier gas passing through said membrane into the patient's blood stream to create a defined bolus of blood gases within said equilibration chamber;
    (e) said equilibration chamber comprising an elongated tortuous path having a high ratio of surface area through which blood gases and carrier gases pass through said permeable membrane to unit volume of carrier gas in said equilibration chamber.

2. A blood gas catheter as defined in claim 1 wherein said elongated tortuous path is a spiral path.

3. A blood gas catheter as defined in claim 2 wherein said high ratio of surface area to unit volume is about 50:1.

4. A blood gas catheter probe having a distal end for introduction into a patient's bloodstream; said catheter probe comprising:
    (a) an inlet having a predetermined cross-sectional area for receiving carrier gas;
    (b) an outlet having a predetermined cross-sectional area for removing carrier gas containing dissolved blood gases;
    (c) an equilibration chamber having an elongated, tortuous path of a minimum predetermined length and a predetermined uniform cross-sectional area connecting between said inlet and said outlet;
    (d) a gas permeable membrane surrounding said equilibration chamber adapted to contact the patient's blood and allow blood gases and carrier gas to pass though said membrane to equilibrate and form a bolus of blood gas within said equilibration chamber, wherein said cross-sectional areas of said inlet, said outlet and said path of said equilibration chamber are substantially equal.

5. A blood gas catheter as defined in claim 4 wherein said substantially equal cross sectional areas is about $2.0 \times 10^{-3}$ mm$^2$.

6. A gas catheter probe having a distal end for introduction into a liquid containing gases, for analyzing gases in said liquid, said catheter probe comprising:
    (a) a capillary inlet for delivering a carrier gas to said catheter probe, said inlet terminating by a predetermined length short of the distal end of said catheter probe,
    (b) a central conduit extending to, at, or near the distal end of said gas catheter probe and having formed therein, a capillary outlet for removing carrier gas and gas to be analyzed from said gas catheter probe,
    (c) a wire wrapped spirally about the outside diameter of said central conduit beginning at the termination of said inlet to the end of said central conduit, (d) a gas permeable membrane affixed to said catheter probe and sealed about said wire to form between said outside diameter of said central conduit and said gas permeable membrane, a spiral tortuous equilibration chamber, said gas permeable membrane comprised of a material allowing equilibration of gases passing there through and into said carrier gas within said equilibration chamber.

7. A blood gas catheter probe as defined in claim 6 wherein said wire has its outer surface of a material that inhibits the condensation of water.

8. A blood gas catheter probe as defined in claim 7 wherein said wire has its outer surface of gold.

9. A blood gas catheter as defined in claim 6 wherein said capillary inlet is an annular inlet of predetermined cross-section area.

10. A blood gas catheter as defined in claim 6 wherein said capillary inlet, said equilibration chamber and said capillary outlet are all of predetermined cross-sectional area and are substantially equal.

11. A blood gas catheter probe as defined in claim 6 wherein said linear length of said catheter probe within which is formed said equilibration chamber is about 2 cm or less.

* * * * *